(12) United States Patent
Kilger

(10) Patent No.: US 8,417,351 B2
(45) Date of Patent: Apr. 9, 2013

(54) PERIPHERAL OXISTIMULATOR APPARATUS AND METHODS

(75) Inventor: Joan M. Kilger, La Crescent, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 12/523,824

(22) PCT Filed: Feb. 8, 2008

(86) PCT No.: PCT/US2008/001670
§ 371 (c)(1),
(2), (4) Date: Jul. 20, 2009

(87) PCT Pub. No.: WO2008/123903
PCT Pub. Date: Oct. 16, 2008

(65) Prior Publication Data
US 2010/0099963 A1    Apr. 22, 2010

Related U.S. Application Data

(60) Provisional application No. 60/900,540, filed on Feb. 9, 2007.

(51) Int. Cl.
*A61N 1/00*    (2006.01)
(52) U.S. Cl.
USPC .......................................................... 607/62
(58) Field of Classification Search ........................ None
See application file for complete search history.

(56) References Cited

U.S. PATENT DOCUMENTS

| 4,440,160 | A | * | 4/1984 | Fischell et al. ................ 128/846 |
| 5,275,159 | A | * | 1/1994 | Griebel ......................... 600/324 |
| 5,423,327 | A | * | 6/1995 | Clauson et al. ............... 600/322 |
| 5,555,891 | A | * | 9/1996 | Eisenfeld ...................... 600/534 |
| 6,935,335 | B1 | * | 8/2005 | Lehrman et al. ......... 128/200.24 |
| 7,025,730 | B2 | * | 4/2006 | Cho et al. ...................... 600/529 |
| 7,155,278 | B2 | * | 12/2006 | King et al. ........................ 607/2 |
| 7,524,292 | B2 | | 4/2009 | Cho et al. |
| 2005/0085868 | A1 | * | 4/2005 | Tehrani et al. .................. 607/42 |
| 2006/0097879 | A1 | | 5/2006 | Lippincott |

(Continued)

FOREIGN PATENT DOCUMENTS

WO    WO 2010/093677 A3    8/2010

OTHER PUBLICATIONS

Benumof, JL, "Creation of Observational Unit May Decrease Sleep Apnea Risk," APSF Newsletter, Letters to the Editor, 2002. [retrieved on Jan. 24, 2011]. Retrieved from the Internet: <URL:http://apsf.org/newsletters/html/2002/fall/07/letterseditor.htm>; 2 pgs.

(Continued)

*Primary Examiner* — Eric D. Bertram
*Assistant Examiner* — Roland Dinga
(74) *Attorney, Agent, or Firm* — Mueting, Raasch & Gebhardt, P.A.

(57) ABSTRACT

Apparatus and methods for monitoring a patient's blood oxygen content (through, e.g., an external finger probe using a pulse oximeter). If the patient's blood oxygen content falls below a selected level, a safe, yet effective, level of peripheral nerve stimulation would be delivered to the patient's wrist in the form of a milliamp current to arouse the patient.

23 Claims, 2 Drawing Sheets

U.S. PATENT DOCUMENTS

| | | | |
|---|---|---|---|
| 2006/0282131 A1* | 12/2006 | Caparso et al. | 607/62 |
| 2007/0167843 A1* | 7/2007 | Cho et al. | 600/484 |
| 2008/0195173 A1 | 8/2008 | Villa | |
| 2010/0286545 A1 | 11/2010 | Wolfe et al. | |

OTHER PUBLICATIONS

Boushra, NN, "Anaesthetic management of patients with sleep apnoea syndrome," *Can. J. Anaesth.*, 1996;43(6):599-616.

Chediak et al., "Obstructive Sleep Apnea Syndrome," *Pulmonary and Critical Care Medicine*, Bone et al., Eds., St. Louis, MO, Part Q, Disorders of the Control of Breathing,1997;2:1-28.

Connolly, LA, "Anesthetic Management of Obstructive Sleep Apnea Patients," *J. Clin. Anesth.*, Nov./Dec. 1991;3:461-469.

Cullen, DJ, "Obstructive Sleep Apnea and Postoperative Analgesia: A Potentially Dangerous Combination," *J. Clin. Anesth.*, 2001;13:83-85.

del Campo et al., "Oxygen saturation regularity analysis in the diagnosis of obstructive sleep apnea," *Artif. Intell. Med.*, 2006;37:111-118.

Esclamado et al., "Perioperative Complications and Risk Factors in the Surgical Treatment of Obstructive Sleep Apnea Syndrome," *Laryngoscope*, Nov. 1989;99:1125-1129.

Flemons, WW, "Obstructive Sleep Apnea," *N. Engl. J.Med.*, Aug. 15, 2002;347(7):498-504.

Hillarp et al., "Videoradiography at Submental Electrical Stimulation During Apnea in Obstructive Sleep Apnea Syndrome. A Case Report," *Acta Radiol.*, 1991: 32(3):256-259.

International Search Report and Written Opinion, issued May 27, 2008, for PCT Patent Application No. PCT/US2008/001670, filed Feb. 8, 2008: 12 pgs.

International Preliminary Report on Patentability, issued Aug. 11, 2009, for PCT Patent Application No. PCT/US2008/001670, filed Feb. 8, 2008: 7 pgs.

Issa et al., "Arousal responses to airway occlusion in sleeping dogs; comparison of nasal and tracheal occlusions," *J. Appl. Physiol.*, 1987;62:1832-1836.

Masimo Corporation, "Breaking Studies: Masimo SET Pulse Oximetry Technology Again Shown to be Most Effective," PR Newswire, New York; Oct. 26, 2006:3 pgs.

Moos et al., "Are Patients with Obstructive Sleep Apnea Syndrome Appropriate Candidates for the Amubulatory Surgical Center?" *AANA Journal*, Jun. 2005; 73(3):197-205.

National Commission on Sleep Disorders Research: *Wake up America: A National Sleep Alert.*, vol. 1, Executive Summary and Executive Report, Jan. 1993:1-76.

Piao et al., "The effects of transcutaneous electrical stimulation during sleep on obstructive sleep apnea," *Clin. J. Tuberc. Respir. Dis.*, Aug. 1998; 21(8)492-493.

Schwartz et al., "Therapeutic Electrical Stimulation of the Hypoglossal Nerve in Obstructive Sleep Apnea," *Arch. Otolaryngol. Head Neck Surg.*, Oct. 2001; 127(10):1216-1223. [retrieved on Jan. 4, 2011]. Retrieved from the Internet: <URL:http://archotol.ama-assn.org.cgi/content/full/127/10/1216>; 12 pgs.

The Doctors Company: Sleep Apnea and Narcotic Postoperative Pain Medication: a Mordibity and Mortality Risk, [retrieved on Jan. 5, 2011]. Retrieved from the Internet: <URL:http://www.thedoctors.com/KnowledgeCenter/PatientSafety/articles/CON_ID_00173:3 pgs.

Young et al. "Estimation of Clinically Diagnosed Proportion of Sleep Apnea Syndrome in Middle-Aged Men and Women," *Sleep*, 1997;20(9):705-706.

Young et al., "Epidemiology of Obstructive Sleep Apnea: a Population Health Perspective," *Am. J. Respir. Crit. Care Med.*, 2002;165:1217-1239.

Zornow, MH, "Clinical Testing of the Apnea Prevention Device: Proof of Concept Data," www.anesthesia-analgesia.org, Mar. 2011; 112(3):582-586.

* cited by examiner

PERIPHERAL OXISTIMULATOR APPARATUS AND METHODS

RELATED APPLICATION

The present application is a U.S. National Stage Application of International Application No. PCT/US2008/001670, titled PERIPHERAL OXISTIMULATOR APPARATUS AND METHODS, filed on Feb. 8, 2008, which claims the benefit under 35 U.S.C. §119 of U.S. Provisional Patent Application Ser. No. 60/900,540 filed on Feb. 9, 2007 and titled PERIPHERAL OXISTIMULATOR APPARATUS AND METHODS, which is hereby incorporated by reference in its entirety.

Obstructive sleep apnea is a potentially fatal condition affecting up to 18 million Americans. The majority of these individuals, 80-95%, remain undiagnosed. Obstructive sleep apnea consists of repeated episodes of partial or complete upper airway obstruction during sleep due to relaxation of the muscles that support the upper airway. These episodes of apnea cause declines in blood oxygen saturation by 4% or more. Arousal ends the obstruction. Central nervous system arousal mechanisms are secondary to chemoreceptor activation and upper airway mechanoreceptors. Extreme episodes of apnea from airway obstruction, which are not ended through arousal, can cause respiratory arrest.

Administration of narcotics or other sedating medications to hospitalized patients who were ultimately diagnosed with OSA, has been associated with respiratory arrest and death. The effects of narcotic analgesia attenuates arousal and awakening, leading to airway obstruction, hypoxemia, and respiratory arrest. Patients with obstructive sleep apnea syndrome (OSAS) appear to be much more vulnerable to apnea than normal individuals under the same level of sedation. This increased tendency of OSAS patients to develop airway obstruction can occur out of proportion to the level of sedation. Many patients who developed an obstructive sleep apnea episode had complained of, and were treated for, significant pain shortly before the episode.

Also complicating safe postoperative pain management of undiagnosed OSAS patients is the increasing number of surgeries done late in the day. Post-op, these patients are frequently transferred from the PACU to a standard nursing floor late in the evening or at night. The patient's level of postoperative pain is most likely to be at its highest when the nurse-to-patient staffing ratio is typically at its lowest.

Hospitalized patients with undiagnosed sleep apnea will continue to be at risk for sudden death unless a system is implemented that can prevent this. Presently, several steps are practiced to reduce the risk of adverse outcomes in hospitalized OSAS patients. The first is identification of patients with undiagnosed OSAS. This is done by a careful exam and history of every patient undergoing anesthesia. This approach can fail in common clinical practice for a variety of reasons. Specifically, a patient's ability to compensate for changes in respiratory controls and mechanics are quite different under the effects of sedation and analgesics than that of normal sleep. Two signs highly correlated with OSAS, snoring and obesity, are common in the general population. Therefore, combinations of clinical variables and patient self-report symptoms have good sensitivity but modest specificity.

After individuals at risk for OSAS are identified, it is common practice to have them monitored postoperatively in an ICU or by pulse oximetry on the floor. Postoperative critical care monitoring of all potential OSAS patients is not feasible due to high cost and limited resources. Audible pulse oximeter monitoring on the floor has limitations. In many of the OSAS medical malpractice cases, an attempt was made to create a middle ground monitoring environment by placing the patient in a room near the nursing station, putting an audible pulse oximeter ($spO_2$) on the finger, and perhaps some sort of apnea alarm monitor on the patient. These monitoring solutions simply did not work; e.g., no nurse passes by the room for many minutes, no one hears the alarms of the pulse oximeter or apnea monitor.

When no reasonable alternatives are available, care providers often are reluctant to give the patient medication for pain hoping to minimize the risk of sudden death. Inadequate pain management for moderate to severe pain is not a humane or satisfactory solution to this problem.

SUMMARY OF THE INVENTION

The present invention provides apparatus and methods for monitoring a patient's blood oxygen content (through, e.g., an external finger probe using a pulse oximeter). Should the patient's blood oxygen content fall below a selected level, a safe, yet effective, level of peripheral nerve stimulation would be delivered to the patient's wrist in the form of a milliamp current to arouse the patient.

The apparatus and methods of the invention would be used as a backup for the patient's own intrinsic mechanism of arousal which may have become obtunded by medication. In various embodiments, the apparatus could combine a pulse oximeter with a peripheral nerve stimulator in one integral unit. The apparatus and methods could be used as an adjunct with other safety precautions for OSA patients.

In one aspect, the present invention provides peripheral oxistimulator apparatus, the apparatus including a blood oxygen saturation monitor; a peripheral nerve stimulator adapted to deliver electrical energy to the skin of a patient; and an interconnect system operatively connecting the blood oxygen saturation monitor and the peripheral nerve stimulator, wherein the peripheral nerve stimulator is activated when oxygen saturation in a patient reaches a selected value.

In various embodiments, the present invention may include one or more of the following: a blood oxygen saturation monitor in the form of a pulse oximeter; a blood oxygen saturation monitor including a sensor, a power source, a control system operatively connected to the sensor and the power source, and a pulse oximeter cable connecting the sensor to the control system; a peripheral nerve stimulator including a power source, an electrical stimulation generator, one or more electrodes adapted to deliver electrical stimulation to the skin of a patient, and a stimulator cable connecting the one or more electrodes to the electrical stimulation generator; a common housing containing the blood oxygen saturation monitor and the peripheral nerve stimulator; a wristband that comprises one or more surface electrodes adapted to deliver electrical stimulation to the skin of a patient wearing the wristband; an external event indicator operatively connected to the control system, wherein the control system activates the external event indicator when the peripheral nerve stimulator is activated; a motion sensor operatively connected to the peripheral nerve stimulator, wherein movement of the patient deactivates the peripheral nerve stimulator; etc.

In another aspect, the present invention provides a method of protecting patients receiving narcotics and/or sedatives from respiratory arrest due to sleep apnea, the method including monitoring blood oxygen saturation levels of a patient using a blood oxygen saturation monitor; and delivering electrical energy to the skin of the patient when the monitored blood oxygen saturation level of the patient falls below a selected level.

In various embodiments, the methods may include one or more of the following: delivering electrical energy using a peripheral nerve stimulator; providing the peripheral nerve stimulator and the blood oxygen saturation monitor in a common housing; monitoring movement of the patient; increasing the duration and/or intensity of the electrical energy delivered to the patient until the patient moves; delivering a signal to a remote monitoring system when electrical energy is delivered to the skin of the patient; using a wristband with the peripheral nerve stimulator that includes one or more surface electrodes adapted to deliver electrical stimulation to the skin of a patient wearing the wristband The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

BRIEF DESCRIPTION OF THE VIEWS OF THE DRAWING

The present invention will be further described with reference to the figures of the drawing, wherein.

DETAILED DESCRIPTION OF EXEMPLARY EMBODIMENTS

Figure 1:
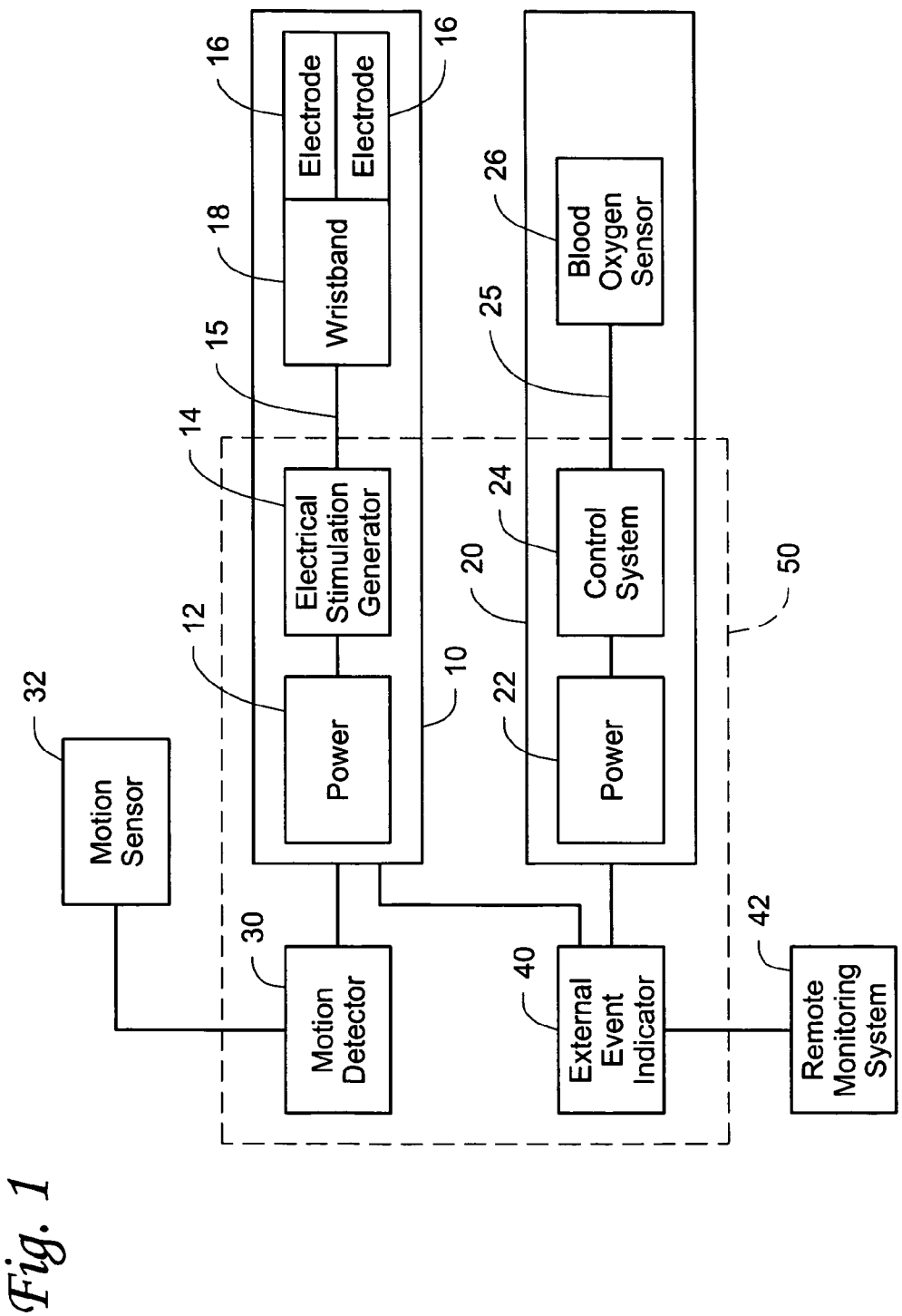
FIG. 1 is a block diagram depicting optional components of one potential system according to the present invention.

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

FIG. 1 depicts one exemplary embodiment of a peripheral oxistimulator according to the present invention. The system includes a peripheral nerve stimulator 10 and a blood oxygen monitor 20. Other optional components also depicted in connection with the exemplary system of FIG. 1 are a motion detector 30 and an external event indicator 40.

The peripheral nerve stimulator 10 may preferably include a power source 12 and an electrical stimulation generator 14, along with electrodes 16 that may preferably be provided on a wristband 18 (other mechanism for attaching the electrodes 16 to a patient) such that electrical energy from the electrical stimulation generator 14 can be delivered to the patient. The electrodes 16 are preferably operably connected to the electrical stimulation generator using a stimulator cable 15.

The electrical stimulation generator 14 is preferably capable of delivering an electric current (e.g., a milliamp current) to the patient's skin that is of sufficient duration and/or intensity to arouse a patient in the event the patient's blood oxygen content falls below a selected level. The electric current is preferably delivered through the electrodes 16 that are preferably retained in contact with the patient's skin.

The blood oxygen monitor 20 may preferably include a power source 22 and control system 24, along with a sensor 26. The components of the blood oxygen saturation monitor are preferably operably interconnected to each other. It may be preferred that the blood oxygen monitor 20 provide a signal in the form of a blood oxygen saturation in percent, although other measurements may be used as an indicator of blood oxygen content.

It may be preferred that at least some components of the peripheral nerve stimulator 10 and the blood oxygen content monitor 20 be located within a common housing 50. The common housing 50 may, for example, contain power sources 12 and 22 for the electrical stimulation generator 14 and the blood oxygen content monitor control system 24, respectively. Although depicted as separate, the power sources 12 and 22 may be shared. Further, the power sources may be self-contained within the housing 50 (e.g., in the form of batteries, fuel cells, capacitive discharge units, etc.). Alternatively, the power sources used by the components may be from a centralized power source (e.g., wall outlets providing 120/220V power.

The blood oxygen monitor 20 may preferably be a non-invasive sensor such as a pulse oximeter. As used herein, the term "pulse oximeter" will include both the optical sensor and the circuitry used to determine blood oxygen saturation levels using the optical sensor. Pulse oximeters may be available form a variety of sources, such as, e.g., Masimo Corporation (Irvine, Calif.). It may be preferred that the sensor 26 of the pulse oximeter be attached to the finger of a patient. Alternative embodiments may employ sensors that attach elsewhere on the body.

While a pulse oximeter is one preferred non-invasive oxygen sensor, it should be understood that any blood oxygen sensor, invasive or non-invasive, useful for determining blood oxygen content levels (preferably continuously) could be used in connection with the present invention. It should also be apparent to those skilled in the art that developing technologies, such as an implantable, micro-electromechanical (MEMS) blood gas analyzer, may provide the blood oxygen content information needed in connection with the present invention. Furthermore, measurements other than oxygen saturation may be used in connection with the present invention, such as, e.g., the level of carboxyhemoglobin, etc.

Blood oxygen content measuring in connection with the present invention may be described as "continuous" although it will be understood that the measurements made using, e.g., pulse oximeters and other devices, may actually be taken at discrete intervals. As discussed above, "continuous" as used in connection with the measuring of blood oxygen content in the present invention includes measurement of the blood oxygen content levels of the patient at intervals (fixed or variable) that are sufficiently small to provide the advantages of the invention. Preferably the sampling intervals will be less than about five minutes, more preferably less than about one minute.

The system of FIG. 1 also includes an optional motion detector 30 that is capable of determining movement by the patient. It may be advantageous to determine, e.g., whether a patient is aroused by delivery of a peripheral nerve stimulation from the peripheral nerve stimulator. If the patient is not aroused (as indicated by, e.g., movement), the duration and/or intensity of the electrical stimulation delivered to the patient may be increased or otherwise changed in an attempt to arouse the patient.

The motion detector 30 may preferably include a motion sensor 32 attached to the patient such that movement by the patient can be sensed. The motion sensor may take any number of a variety of forms, e.g., an accelerometer, attitude sensor, etc.

Also included in the system of FIG. 1 is an external event indicator 40 that may preferably be capable of delivering a signal to a remote monitoring system 42 when the blood oxygen content of a patient has fallen below a selected level such that electrical stimulation is being delivered to the patient. The remote monitoring system 42 may be, e.g., a nursing station, etc. that is in a location removed from the immediate vicinity of the patient.

The systems of the present invention may also be capable of storing data indicative of the patient's blood oxygen content, the number of times peripheral nerve stimulation is delivered, the duration/intensity of any peripheral nerve stimulation, etc. The data may be stored within one or more components of the system (e.g., the peripheral nerve stimulator 10, blood oxygen monitor 20, etc.). Alternatively (or in addition to on-board storage), the data may be transmitted to a remote monitoring system for storage if a remote monitoring system is used in connection with the invention.

Figure 2:
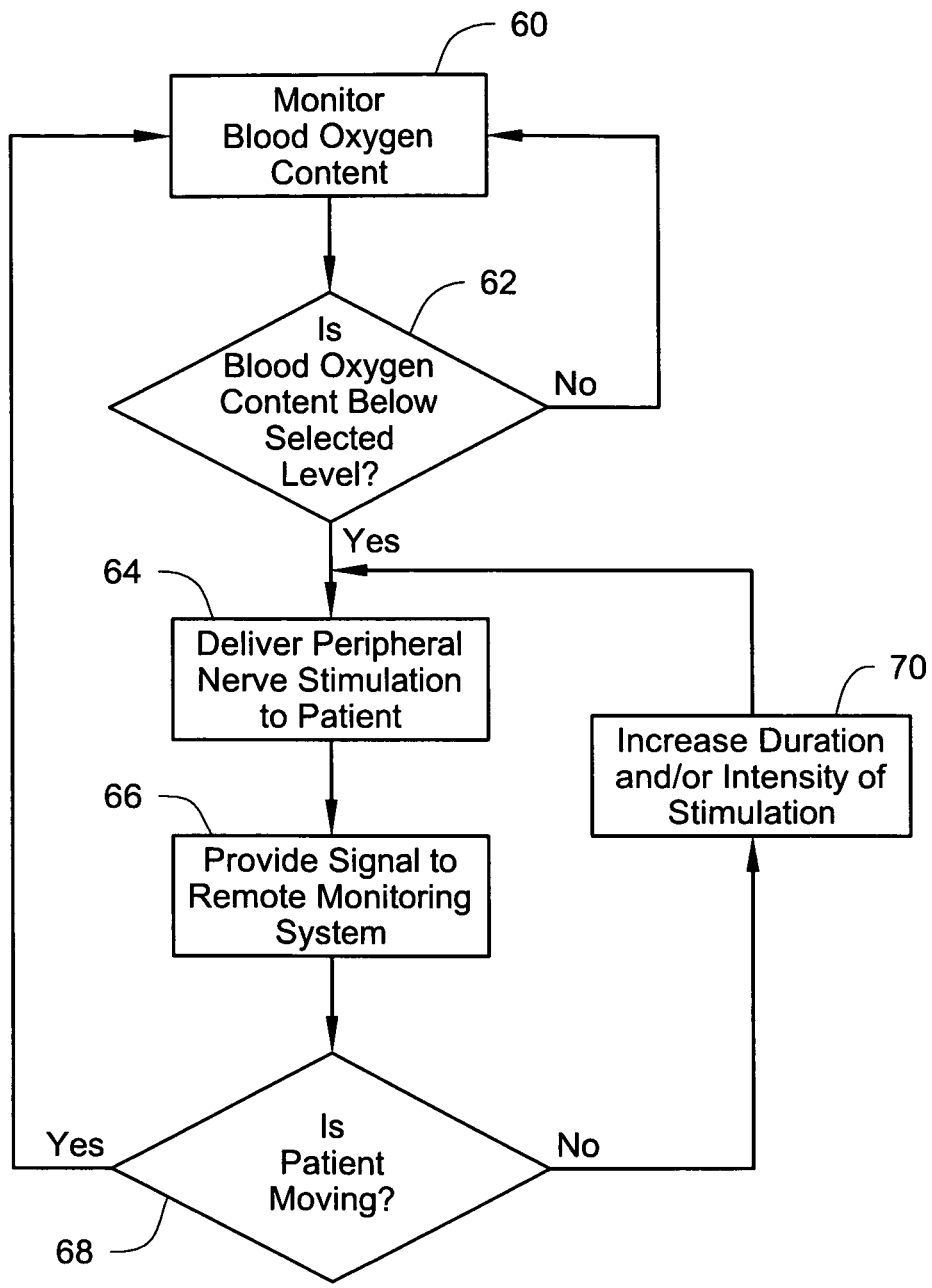
FIG. 2 is a flow diagram depicting activities in one exemplary method according to the present invention.

FIG. 2 is a flow diagram of one exemplary method according to the present invention. As discussed herein, the method of the invention may be advantageously practiced in connection with sleeping patients who have been administered narcotics and/or sedatives as a back-up for their intrinsic arousal mechanisms (which may have been obtunded by the medications) in the event of a sleep apnea incident.

The method involves monitoring blood oxygen content 60 by any suitable technique. Typically, the user (doctor, nurse, etc.) will set the level at or above which blood oxygen content should be maintained. If (as indicated by decision box 62) the patient's blood oxygen content falls below the selected level, then peripheral nerve stimulation may preferably be delivered to the patient (as indicated at box 64). If the monitored blood oxygen content level is at or above the selected value, then the system would continue monitoring blood oxygen content levels.

Some optional activities are also depicted in the flow diagram of FIG. 2. Among the optional activities is the one depicted in box 66, where a signal is provided to a remote monitoring system to provide an indication that the patient's blood oxygen content has fallen below the selected level and/or that peripheral nerve stimulation has been delivered to the patient.

Another optional activity included in the method depicted in the flow diagram of FIG. 2 is determining whether the patient is moving after electrical stimulation has been delivered to them (decision box 68). Motion detection may be may be carried out by any suitable technique. One potentially preferred technique is through the use of a motion sensor attached to the patient. The motion sensor may take the form of an accelerometer, inclinometer, etc. as are known in the art. Changes in acceleration or inclination of the sensor can be used to indicate that the patient has been aroused and moved (typically in response to the peripheral nerve stimulation).

If the patient has moved, then the method may preferably involve returning to the monitoring of patient blood oxygen content as indicated in box 60. If the patient has not moved in response to the peripheral nerve stimulation, then the method may preferably involve increasing the duration and/or intensity of the peripheral nerve stimulation (box 70) in an attempt to arouse the patient.

The complete disclosure of any patents, patent documents, and publications cited in the Background, the Detailed Description of Exemplary Embodiments, and elsewhere herein are incorporated by reference in their entirety as if each were individually incorporated.

Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A peripheral oxistimulator apparatus, the apparatus comprising:
    a blood oxygen saturation monitor;
    a peripheral nerve stimulator adapted to deliver electrical energy to the skin of a patient;
    an interconnect system operatively connecting the blood oxygen saturation monitor and the peripheral nerve stimulator, wherein the peripheral nerve stimulator is activated when oxygen saturation in a patient reaches a selected value; and
    a motion sensor operatively connected to the peripheral nerve stimulator, wherein movement of the patient deactivates the peripheral nerve stimulator;
    and wherein the peripheral oxistimulator apparatus is configured to increase the duration of the electrical energy delivered to the skin of the patient as compared to the duration of electrical energy previously delivered as peripheral nerve stimulation if the patient does not move in response to the previously delivered peripheral nerve stimulation.

2. An apparatus according to claim 1, wherein the blood oxygen saturation monitor comprises a pulse oximeter.

3. An apparatus according to claim 2, wherein the blood oxygen saturation monitor comprises a sensor, a power source, a control system operatively connected to the sensor and the power source, and a pulse oximeter cable connecting the sensor to the control system.

4. An apparatus according to claim 1, and wherein the peripheral nerve stimulator comprises a power source, an electrical stimulation generator, one or more electrodes adapted to deliver electrical stimulation to the skin of a patient, and a stimulator cable connecting the one or more electrodes to the electrical stimulation generator.

5. An apparatus according to claim 1, wherein the blood oxygen saturation monitor comprises a sensor, a power source, a control system operatively connected to the sensor and the power source, and a pulse oximeter cable connecting the sensor to the control system, and wherein the peripheral nerve stimulator comprises a power source, an electrical stimulation generator, one or more electrodes adapted to deliver electrical stimulation to the skin of a patient, and a stimulator cable connecting the one or more electrodes to the electrical stimulation generator.

6. An apparatus according to claim 5, wherein the blood oxygen saturation monitor and the peripheral nerve stimulator share a common housing.

7. An apparatus according to claim 6, wherein the common housing contains the power source for the blood oxygen saturation monitor and the power sources for the peripheral nerve stimulator.

8. An apparatus according to claim 1, wherein the peripheral nerve stimulator comprises a wristband that comprises one or more surface electrodes adapted to deliver electrical stimulation to the skin of a patient wearing the wristband.

9. An apparatus according to claim 1, further comprising an external event indicator comprising a signal generator delivering a signal to a remote monitoring system when the peripheral nerve stimulator is activated.

10. An apparatus according to claim 1, wherein the motion sensor is configured for attachment to the patient.

11. An apparatus according to claim 1, wherein the motion sensor comprises an accelerometer.

12. A peripheral oxistimulator apparatus, the apparatus comprising:
a blood oxygen saturation monitor;
a peripheral nerve stimulator adapted to deliver electrical energy to the skin of a patient;
an interconnect system operatively connecting the blood oxygen saturation monitor and the peripheral nerve stimulator, wherein the peripheral nerve stimulator is activated when oxygen saturation in a patient reaches a selected value; and
a motion sensor operatively connected to the peripheral nerve stimulator, wherein movement of the patient deactivates the peripheral nerve stimulator;
and wherein the peripheral oxistimulator apparatus is configured to increase the intensity of the electrical energy delivered to the skin of the patient as compared to the intensity of electrical energy previously delivered as peripheral nerve stimulation if the patient does not move in response to the previously delivered peripheral nerve stimulation.

13. An apparatus according to claim 12, and wherein the peripheral nerve stimulator comprises a power source, an electrical stimulation generator, one or more electrodes adapted to deliver electrical stimulation to the skin of a patient, and a stimulator cable connecting the one or more electrodes to the electrical stimulation generator.

14. An apparatus according to claim 12, wherein the blood oxygen saturation monitor comprises a sensor, a power source, a control system operatively connected to the sensor and the power source, and a pulse oximeter cable connecting the sensor to the control system, and wherein the peripheral nerve stimulator comprises a power source, an electrical stimulation generator, one or more electrodes adapted to deliver electrical stimulation to the skin of a patient, and a stimulator cable connecting the one or more electrodes to the electrical stimulation generator.

15. An apparatus according to claim 12, wherein the peripheral nerve stimulator comprises a wristband that comprises one or more surface electrodes adapted to deliver electrical stimulation to the skin of a patient wearing the wristband.

16. An apparatus according to claim 12, further comprising an external event indicator comprising a signal generator delivering a signal to a remote monitoring system when the peripheral nerve stimulator is activated.

17. An apparatus according to claim 12, wherein the motion sensor is configured for attachment to the patient.

18. A peripheral oxistimulator apparatus, the apparatus comprising:
a blood oxygen saturation monitor;
a peripheral nerve stimulator adapted to deliver electrical energy to the skin of a patient;
an interconnect system operatively connecting the blood oxygen saturation monitor and the peripheral nerve stimulator, wherein the peripheral nerve stimulator is activated when oxygen saturation in a patient reaches a selected value; and
a motion sensor operatively connected to the peripheral nerve stimulator, wherein movement of the patient deactivates the peripheral nerve stimulator;
and wherein the peripheral oxistimulator apparatus is configured to increase the duration and the intensity of the electrical energy delivered to the skin of the patient as compared to the duration and intensity of electrical energy previously delivered as peripheral nerve stimulation if the patient does not move in response to the previously delivered peripheral nerve stimulation.

19. An apparatus according to claim 18, and wherein the peripheral nerve stimulator comprises a power source, an electrical stimulation generator, one or more electrodes adapted to deliver electrical stimulation to the skin of a patient, and a stimulator cable connecting the one or more electrodes to the electrical stimulation generator.

20. An apparatus according to claim 18, wherein the blood oxygen saturation monitor comprises a sensor, a power source, a control system operatively connected to the sensor and the power source, and a pulse oximeter cable connecting the sensor to the control system, and wherein the peripheral nerve stimulator comprises a power source, an electrical stimulation generator, one or more electrodes adapted to deliver electrical stimulation to the skin of a patient, and a stimulator cable connecting the one or more electrodes to the electrical stimulation generator.

21. An apparatus according to claim 18, wherein the peripheral nerve stimulator comprises a wristband that comprises one or more surface electrodes adapted to deliver electrical stimulation to the skin of a patient wearing the wristband.

22. An apparatus according to claim 18, further comprising an external event indicator comprising a signal generator delivering a signal to a remote monitoring system when the peripheral nerve stimulator is activated.

23. An apparatus according to the claim 18, wherein the motion sensor is configured for attachment to the patient.

* * * * *